(12) United States Patent
Yang et al.

(10) Patent No.: US 9,596,992 B2
(45) Date of Patent: Mar. 21, 2017

(54) INTELLIGENT NURSING CARE DEVICE

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Jiuxia Yang, Beijing (CN); Feng Bai, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 11 days.

(21) Appl. No.: 14/416,034

(22) PCT Filed: May 6, 2014

(86) PCT No.: PCT/CN2014/076851
§ 371 (c)(1),
(2) Date: Jan. 20, 2015

(87) PCT Pub. No.: WO2015/089979
PCT Pub. Date: Jun. 25, 2015

(65) Prior Publication Data
US 2016/0038026 A1 Feb. 11, 2016

(30) Foreign Application Priority Data
Dec. 16, 2013 (CN) .......................... 2013 1 0688758

(51) Int. Cl.
*A61B 5/00* (2006.01)
*A61B 5/11* (2006.01)
(Continued)

(52) U.S. Cl.
CPC .............. *A61B 5/0022* (2013.01); *A61B 5/00* (2013.01); *A61B 5/002* (2013.01); *A61B 5/0046* (2013.01);
(Continued)

(58) Field of Classification Search
CPC ..... A61B 5/0002; A61B 5/11; A61B 5/02438; A61B 5/0024; A61B 5/1113;
(Continued)

(56) References Cited

U.S. PATENT DOCUMENTS

2010/0274104 A1  10/2010  Khan
2010/0324936 A1*  12/2010  Vishnubhatla ........ G06F 19/322
                                                    705/3
(Continued)

FOREIGN PATENT DOCUMENTS

CN    101257513 A    9/2008
CN    101732041 A    6/2010
(Continued)

OTHER PUBLICATIONS

Chinese Office Action dated Jan. 27, 2015 regarding Application No. 201310688758.4, filed Dec. 16, 2013. Translation provided by Dragon Intellectual Property Law Firm.
(Continued)

*Primary Examiner* — Van Trieu
(74) *Attorney, Agent, or Firm* — Harness, Dickey & Pierce, P.L.C.

(57) ABSTRACT

The present disclosure discloses an intelligent nursing care device, which is a wearable nursing care device and comprises a monitoring unit that acquires a position information and a health condition information of a wearer in real time, and a control unit that determines, based on the position information and the health information acquired by the monitoring unit, a safety condition and a health condition of the wearer, and transmits a determination result to at least one of a cloud server and a monitoring terminal. By wearing
(Continued)

the intelligent nursing care device, an intelligent nursing care service and safety tracking service are provided to a wearer.

8 Claims, 7 Drawing Sheets

(51) Int. Cl.
   *G01S 19/40* (2010.01)
   *G06F 19/00* (2011.01)
(52) U.S. Cl.
   CPC ............ *A61B 5/1112* (2013.01); *A61B 5/1113* (2013.01); *A61B 5/741* (2013.01); *A61B 5/746* (2013.01); *G01S 19/40* (2013.01); *G06F 19/3475* (2013.01)
(58) Field of Classification Search
   CPC ..... A61B 5/1115; A61B 5/1128; A61B 5/746; A61B 5/0004; A61B 5/112
   See application file for complete search history.

(56) References Cited

U.S. PATENT DOCUMENTS

| | | | | |
|---|---|---|---|---|
| 2013/0173285 A1* | 7/2013 | Hyde | ................... | G06F 19/322 705/2 |
| 2014/0350720 A1* | 11/2014 | Lehmann | ............ | G06F 19/3462 700/236 |
| 2015/0026647 A1* | 1/2015 | Park | ...................... | G06F 3/0488 715/863 |
| 2015/0112151 A1* | 4/2015 | Muhsin | .................. | A61B 5/002 600/301 |

FOREIGN PATENT DOCUMENTS

| | | |
|---|---|---|
| CN | 102038548 A | 5/2011 |
| CN | 102614084 A | 8/2012 |
| CN | 203122372 U | 8/2013 |
| CN | 203133495 U | 8/2013 |
| CN | 203178681 U | 9/2013 |
| CN | 103402005 A | 11/2013 |
| CN | 103417202 A | 12/2013 |
| CN | 203314940 U | 12/2013 |
| CN | 103690285 A | 4/2014 |
| KR | 20120094590 A | 8/2012 |
| WO | 03079307 A1 | 9/2003 |

OTHER PUBLICATIONS

Written Opinion of the International Searching Authority for international application No. PCT/CN2014/076851, Jul. 2009.

* cited by examiner

INTELLIGENT NURSING CARE DEVICE

CROSS-REFERENCE TO RELATED APPLICATION

This application is the U.S. national phase of PCT Application No. PCT/CN2014/076851 filed on May 6, 2014, which claims priority to Chinese Patent Application No. 201310688758.4 filed on Dec. 16, 2013, the disclosures of which are incorporated in their entirety by reference herein.

TECHNICAL FIELD

The present disclosure relates to the field of intelligent device, in particular to an intelligent nursing care device.

BACKGROUND

Currently, in our country, nursing care for elderly people is a serious problem. From individual to country, nursing care for elderly people is an important social problem to be solved. A key in the nursing care for elderly people is that the elderly people lose the ability to work, memory continues to decline with an increase of age. Some elderly people also lose normal sense of judgment, such as forgetting the way back to home after an outgo, and this may easily cause a get-lost of the elderly people. Some elderly people need medicine to deal with some unexpected or persistent disease. If no one reminds a dosage of the medicine, the elderly people may forget to take medication. The elderly people may even mistake a dosage method and amount of the medicine and may cause a great harm to the life. With an increase of aging population, it becomes more difficult for the children to take care of the elderly people by their sides.

According to a prior art, a self-reminder card is suggested for a going out of the elderly people. This self-reminder card is a card type reminder device, and is able to remind the elderly people by outputting a speech notification when the elderly people forget some matters and the matters need to be reminded to the elderly people.

Above-described card only can provide the speech notification that is preliminarily stored, but cannot provide a more comprehensive intelligent help to the elderly people who has no helper around him or her. Thus, family members of the elderly people cannot promptly acquire the health condition of the elderly people. This problem is not limited to the elderly people, other groups of people may also have similar problems.

SUMMARY (1) Problem to be Solved

A problem to be solved by the present disclosure is to provide an intelligent help and care service to a person so that a family member of the person can acquire a health condition of the person in real time.

(2) Technical Method

In order to solve the above-described technical problem, the present disclosure provides an intelligent nursing care device. The intelligent nursing care device is a wearable nursing care device. The nursing care device includes:

a monitoring unit that acquires a position information and a health condition information of a wearer in real time; and a control unit that determines, based on the position information and the health information acquired by the monitoring unit, a safety condition and a health condition of the wearer, and transmits a determination result to a cloud server and/or a monitoring terminal.

Further, the monitoring unit includes an electronic fence and a biosensor, the electronic fence includes a camera and a positioning module, and the electronic fence acquires in real time the position information of the wearer at a current time, and the biosensor monitors a human body of the wearer in order to acquire the health condition information of the wearer.

Further, the biosensor is disposed on a back plate that is directly contacted with the human body, and the health condition information is acquired in real time via the biosensor.

Further, the control unit determines the position information acquired by the positioning module, when determining that the position information exceeds a predetermined safety range, the control unit generates a first alarm signal. The control unit further compares the health condition information acquired by the biosensor with a normal health index stored in a database. When the health condition information exceeding the normal health index, the control unit generates a second alarm signal.

Further, the control unit outputs a warning tone simultaneously with a generation of the first alarm signal. After generating the second alarm signal, the control unit automatically transmits the health condition information at the current time to the cloud server and the monitoring terminal.

Further, when the control unit does not generate the second alarm signal, the control unit periodically transmits the health condition information acquired by the biosensor to the cloud server, and the control unit communicates with the cloud server in a wireless manner.

Further, the smart nursing care device includes an online pharmacy unit. The online pharmacy unit includes a communication module and a display panel. The online pharmacy unit communicates with the remote pharmacy system via the communication module, and displays a medicine dosage instruction provided by a remote pharmacy system on the display panel. The medicine dosage instruction includes a medicine type, amount, a medicine taking time, and a medicine taking frequency.

Further, the online pharmacy unit further includes a speech generation device. The online pharmacy unit determines, based on an actual dosage situation acquired by the camera of the monitoring unit, whether the actual dosage situation coincides with the medicine dosage instruction displayed on the display panel. When the actual dosage situation does not perfectly coincide with the medicine dosage instruction, the speech generation device outputs a notification speech until the actual dosage situation perfectly coincides with the medicine dosage instruction.

Further, the positioning module further has a navigation function. When acquiring the position information of the wearer at the current time and a destination together with the camera, the positioning module provides a scheduled route that guides the wearer to the destination based on the position information of the wearer at the current time.

Further, the positioning module acquires the position information of the wearer at the current time, and the position module takes a screenshot of an image taken by the camera and periodically transmits the screenshot to the monitoring terminal.

(3) Advantages

According to an embodiment of the present disclosure, an intelligent nursing care device is provided. The intelligent nursing care device is a wearable nursing care device, and includes a monitoring unit that acquires a position information and a health condition information of a wearer in real time, and a control unit that determines, based on the position information and the health information acquired by the monitoring unit, a safety condition and a health condition of the wearer, and transmits a determination result to a cloud server and/or a monitoring terminal. By wearing the intelligent nursing care device, an intelligent nursing care service and safety tracking service are provided to a wearer. The monitoring unit monitors the position information and the health condition information of the wearer, and the control unit determines the safety condition and the health condition of the wearer. When an activity range of the wearer exceed a safety activity range or a health condition information of the wearer exceed a normal health index, the control unit transmits an alarm signal to a family member holding the monitoring terminal in a timely manner. Thus, an intelligent, accurate, and real time nursing care service can be provided by the intelligent nursing care device.

DETAILED DESCRIPTION

The following will describe embodiments of the present disclosure with reference to specific embodiments and accompanying drawings. It is to be understood that the embodiments shown below are used to explain the present disclosure, but not intend to limit the present disclosure.

Figure 1:
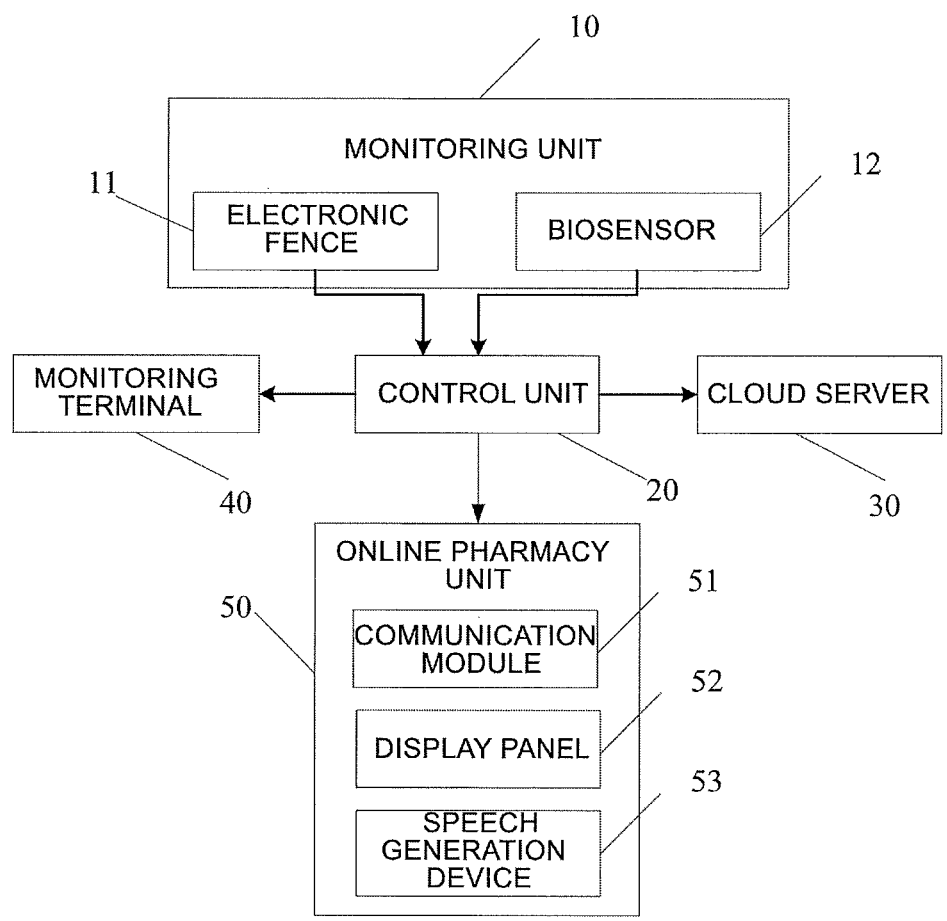
FIG. 1 is a diagram showing a configuration of an intelligent nursing care device according to an embodiment of the present disclosure.

An intelligent nursing care device is provided by an embodiment of the present disclosure. As shown in FIG. 1, the intelligent nursing care device includes a monitoring unit 10 and a control unit 20.

The monitoring unit 10 acquires a position information and a health condition information in real time. The control unit 20 determines, based on the position information and the health information acquired by the monitoring unit 10, a safety condition and a health condition of the wearer, and transmits a determination result to a cloud server 30 and/or a monitoring terminal 40.

The above-described intelligent nursing care device, based on a modern digital technology, provides a remote monitoring service and a medical service to elderly people who live alone. The intelligent nursing care device monitors an activity range and health condition of the elderly people who wear the intelligent nursing care device and acquires health condition information and safety information of the elderly people who live alone in real time in order to provide a broader and intelligent nursing care service to the elderly people.

Alternatively, in the present embodiment, the monitoring unit 10 includes an electronic fence 11 and a biosensor 12. The electronic fence 11 includes a camera and a positioning module. The camera and the positioning module acquire in real time the position information of the wearer at a current time. The biosensor 12 monitors a human body of the wearer in order to acquire the health condition information of the wearer.

Figure 2:
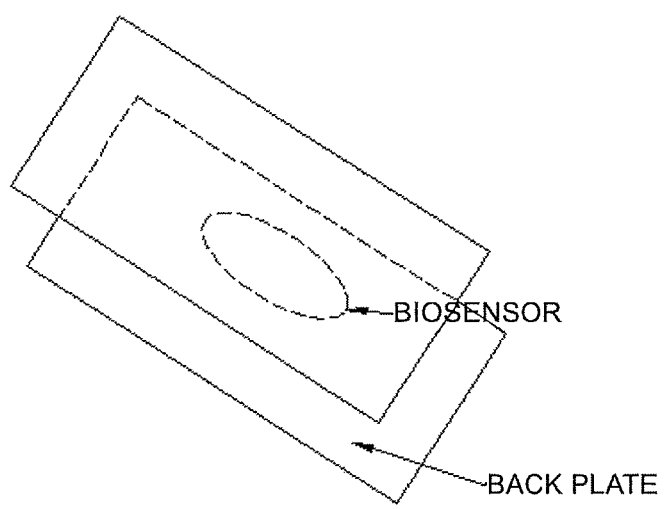
FIG. 2 is a diagram showing a position relation between a back plate and a biosensor according to an embodiment of the present disclosure.

The biosensor 12 is disposed on a back plate that is directly contacted with the human body, and the health condition information is acquired in real time via the biosensor. A position relation of the back plate and the biosensor is shown in FIG. 2. Specifically, in the present embodiment, the health condition information includes information, such as a body temperature, blood pressure, a heart rate, and these multiple kinds of information are stored in a memory.

Alternatively, in the present embodiment, the control unit 20 determines the position information acquired by the positioning module. When determining that the position information exceeds a predetermined safety range, the control unit generates a first alarm signal. The control unit further compares the health condition information sensed by the biosensor 12 with a normal health index stored in a database. When the health condition information exceeds the normal health index, the control unit generates a second alarm signal.

Alternatively, in the present embodiment, the control unit 20 outputs a warning tone simultaneously with a generation of the first alarm signal. After generating the second alarm signal, the control unit 20 automatically transmits a health condition information at the current time to the cloud server 30 and the monitoring terminal 40.

Alternatively, in the present embodiment, when the control unit 20 does not generate the second alarm signal, the control unit 20 periodically transmits the health condition information acquired by the biosensor 12 to the cloud server 30. The control unit 20 performs a wireless communication with the cloud server 30.

Alternatively, in the present embodiment, the intelligent nursing care device further includes an online pharmacy unit 50. The online pharmacy unit 50 includes a communication module 51 and a display panel 52. The online pharmacy unit 50 communicates with the remote pharmacy system via the communication module, and displays a medicine dosage instruction provided by the remote pharmacy system on the display panel 52. The medicine dosage instruction includes a medicine type, amount, a medicine taking time, and a medicine taking frequency.

Alternatively, in the present embodiment, the online pharmacy unit 50 further includes a speech generation device 53. The online pharmacy unit 50 determines, based on an actual dosage situation acquired by the camera of the monitoring unit 10, whether the actual dosage situation coincides with the medicine dosage instruction displayed on the display panel. When the actual dosage situation does not perfectly coincide with the medicine dosage instruction, the speech generation device outputs a notification speech until the actual dosage situation perfectly coincides with the medicine dosage instruction.

Alternatively, in the present embodiment, the positioning module further has a navigation function. When acquiring the position information of the wearer at the current time and a destination together with the camera, the positioning module provides a scheduled route that guides to the destination to the wearer based on the position information of the wearer at the current time.

Alternatively, in the present embodiment, the position module acquires the position information of the wearer at the current time, and the position module takes a screenshot of an image taken by the camera and periodically transmits the screenshot to the monitoring terminal.

The following will describe a best implementation mode of the above-described intelligent nursing care device. In the following example, the monitoring unit is an internet of things system, and the biosensor 12 is a sensor that is specifically prepared for monitoring various parameters of health condition of the human body. Since the biosensor 12 is directly contacted with the human body via the back plate, the biosensor 12 can measure various parameters of the human body. The camera and the positioning module configure the electronic fence 11, and the electronic fence 11 monitors an activity range of the wearer. When detecting that each information of the wearer exceeds a preset range of the electronic fence 11, the control unit 20 generates the first alarm signal, and transmits the alarm signal to the monitoring terminal. The family member of the wearer can obtain, via the monitoring terminal 40, each information of the wearer in real time. Herein, the information includes both the position information and the health condition information.

The control unit 20 carries out the following operations after receiving each information transmitted from the monitoring unit 10.

(1) When the wearer exceeds a range of the electronic fence 11 based on a processing of the position information by the control unit 20, the control unit generates the first alarm signal, that is, a position alarm. Then, the control unit 20 notifies the information to the user by outputting a warning speech. Alternatively, the alarm information and the current position information may be transmitted to the monitoring terminal 40.

(2) When an abnormality occurs in the health condition information based on a processing of the health condition information by the control unit 20, for example, a relatively high blood pressure, the control unit 20 generates the second alarm signal, that is, a health trouble signal. In other words, when a detection result exceeds one predetermined standard of the electronic fence, the detection result may deviate from the normal health index. In response of this deviation, the control unit 20 transmits the alarm signal and the current health condition information to the monitoring terminal 40 held by the family member in order to notify the family member to pay attention to the alarm signal. At the same time, the control unit may transmit the health condition information to the cloud server 30 via a wifi (registered trademark), so that a medical professional person at the remote server can handle a remote medical treatment by referring to the health condition information.

In this process, the health condition information that has been acquired is compared with the normal health index that is stored in a database. When the health condition information exceeds the normal health index, the second alarm signal is generated.

Figure 3:
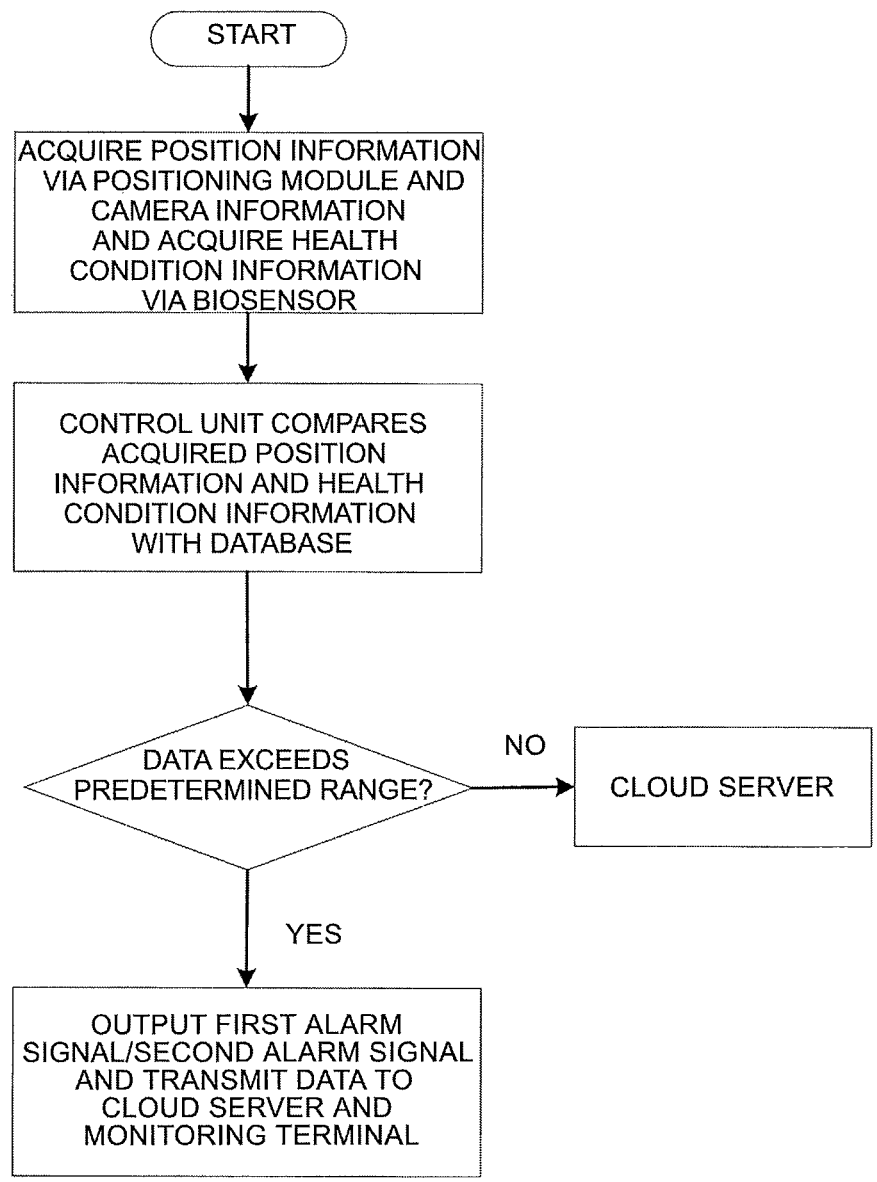
FIG. 3 is a flowchart showing an information processing executed by a control unit when receiving information transmitted from a monitoring unit according to an embodiment of the present disclosure.

(3) Although the biosensor 12 detects that the human body is in a normal state, the control unit 20 periodically transmits the health condition information to the cloud server 30 at predetermined time intervals so that the medical professional person at the remote server is able to monitor the health condition of the wearer as shown in FIG. 3. At this time, since the health condition information of the wearer is within the healthy range, the health condition information needs to be transmitted only to the cloud server 30, but not to the family member of the wearer.

The intelligent nursing care device provided by the present embodiment can provide a monitoring service to both the macro position information and the micro health condition information of the wearer, and provides an intelligent monitoring service to a medicine taking of the wearer, and instructs and reminds the wearer to take the medicine. Thus, the intelligent nursing care device further includes an online pharmacy unit 50. The online pharmacy unit 50 communicates with the remote pharmacy system via a communication module 51. The communication module 51 may be a radio frequency module (that is, RF module) or may be a ZigBee module, or a module that is able to perform a wireless communication. In the present embodiment, RF module will be described as an example. First, the online pharmacy unit 50 receives, via the RF module, data transmitted from the remote pharmacy system. The data includes actual medicine image and dosage amount of the medicine. For example, three pills of Caltrates at one time. The information transmitted from the RF module to the control unit is displayed on the display panel 52. An Image of the medicine pill is displayed together with the text description of the medicine. That is, both the image and the text description are displayed. The display panel 52 further displays the specific medicine taking time and the medicine taking frequency by text description. The contents displayed on the display panel 52 should be suitable to be read by the elderly people. Thus, usually, a large font size is used to display the text description, or a zoom-in function is provided to the display panel 52. In the present embodiment, the display panel 52 is a touch panel in order to provide a convenient operation. It is necessary to explain that, when multiple kinds of medicines need to be taken at one time, the control unit 20 successively receives reminders from the remote pharmacy system. When the control unit detects, via the camera of the nursing care device, a situation that the user takes the medicine exactly according to the instructed types and amounts, the nursing care device ends the current receiving process. Based on the synchronized image captured by the camera, the actual medicine type and medicine amount taken by the wearer can be monitored and can be determined whether the medicine type and the medicine amount are exactly correspond to the instruction. Further, whether a medicine taking interval from the last time taking corresponds to the instruction can be determined. When one check item does not coincide with the instruction, the control unit 20 outputs an alarm signal until the wearer correctly takes the medicine. With this configuration, a proper instruction can be performed to the elderly people for taking the medicine, and can avoid harm to the life caused by an incorrect taking of medicine. Specifically, failing of the medicine taking at predetermined time can be warned by the speech generation device. Further, an image captured by the camera can be compared with information transmitted from the remote pharmacy system in order to provide an instructive speech reminder to the elderly people. For example, when the medicine amount is not correct by comparing a camera captured image of the medicine actually taken by the wearer with the medicine dosage reminder information transmitted from the remote pharmacy system, the intelligent reminder and instruction such as speech reminder of "amount error" or the like can be output to the wearer to instruct the correct taking of the medicine.

Thus, a function of the medicine dosage reminder is provided based on an actual needs and dosage information confirmed by a doctor and received via the radio frequency unit, and the dosage information is reminded to the user using images and speech. This function is different from an alarm function of a mobile phone at the following points. The alarm on the mobile phone needs to be set by the user himself or herself. The medicine dosage reminder in the present embodiment is acquired by a system after confirmation by a professional doctor. Thus, the medicine dosage reminder cannot be modified or canceled. With this configuration, a medicine taking safety of the elderly people can be secured.

Figure 4:
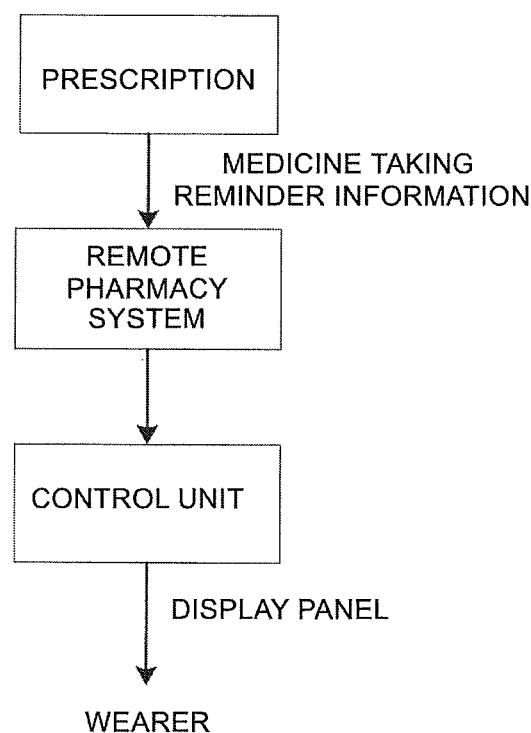
FIG. 4 is a flowchart showing a transmission process executed when medicine dosage reminder information provided by a remote pharmacy system is acquired via a radio frequency module according to an embodiment of the present disclosure.
Figure 5:
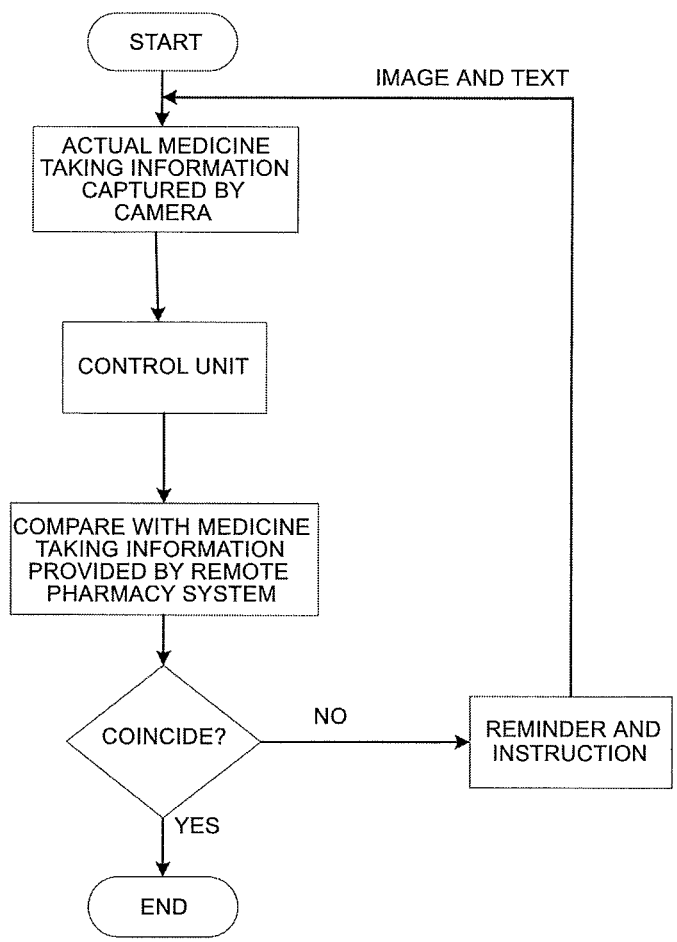
FIG. 5 is a flowchart showing an operation process executed for achieving a medicine dosage reminder function by a control unit and a camera according to an embodiment of the present disclosure.

Based on the above description, the wearer acquires, via the radio frequency module, the medicine dosage reminder information provided by the remote pharmacy system, and a specific flowchart of this process is shown in FIG. 4. When the medicine dosage reminder function starts, the camera activates an image capturing function. When the actual medicine taking information captured by the camera is different from the medicine dosage reminder information, a speech alarm is output to the wearer until the wearer correctly takes the medicine according to the medicine dosage reminder information. This function is achieved by a combined operation of the control unit and the camera. The detailed flowchart of the operation is shown in FIG. 5.

For example, when the user is not in a good health condition, some kinds of medicines need to be taken at predetermined time intervals. In order to avoid a mistake when taking the medicine, when prescribing the medicine, the doctor may transmit related medicine taking information and related medicine taking time to the nursing care device system via the radio frequency unit of the system. The intelligent nursing care device of the user receives the information including detailed information, images, amount, medicine taking time and medicine taking frequency of the related medicine. The information is prescribed by the doctor after confirmation. Thus, the user can receive the related reminder at the predetermined time according to the specific requirement of the doctor. Thus, an accurate and timely taking of medicine by the user can be secured.

Figure 6:
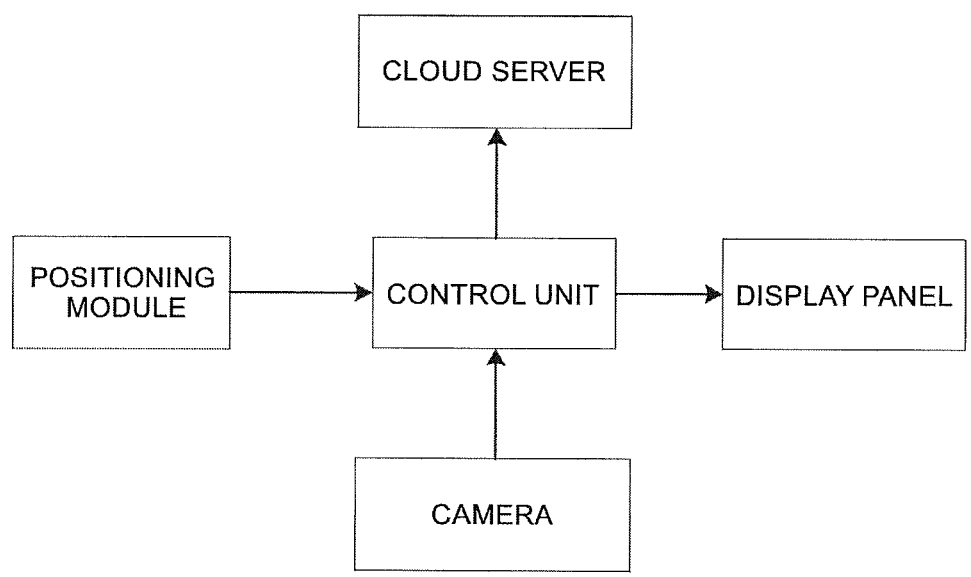
FIG. 6 is a block diagram showing an operation principle for achieving an accurate positioning according to an embodiment of the present disclosure.

The intelligent nursing care device according to the present embodiment further provides a navigation function. The achieving of the navigation function needs to be combined with the position module and the camera. The positioning module accurately specifies an actual position of the wearer based on GPS, and the camera monitors and captures image information of surrounding environment, and transmits the image information to the monitoring terminal 40 via the control unit 20. Thus, the family member can confirm the actual position of the wearer. Further, a place that is usually visited by the wearer can be input to the system. When the wearer needs to go to one place that is usually visited by the wearer, the wearer just needs to input the place using speech input mode. This can improve a use convenience for the elderly people. When the control unit receives the command from the user, the positioning function and the navigation function are activated. Herein, a principle of the navigation function is similar to a navigation function used in a vehicle. However, specific setting and database are different from the in-vehicle navigation function. A GPS database of the intelligent nursing care device according to the present disclosure has more detailed information compared with the in-vehicle navigation, and the GPS system of the present disclosure operates together with the radio frequency module and the camera in order to specify the detailed position information of the user. Then, related information is displayed on the display panel 52 in real time. At the same time, the information is transmitted to the monitoring terminal 40 via the radio frequency module. Herein, the monitoring terminal 40 is placed at the family member end. With this configuration, the family member can obtain a going out of the wearer, and is able to monitor a safety monitoring to the wearer. At the same time, the information related to the position of the wearer during the going out can be confirmed by the family member that is not accompanying the wearer. The detailed operation of this process is shown in FIG. 6.

When the control unit receives a speech information input related to a destination from the user, the control unit promptly activates related function units which include the positioning module, the radio frequency module, and the camera. At this time, each of these modules or devices starts operation. Specifically, the positioning module starts a positioning and navigation state. The RF module and the camera start to capture information, and feedback the information that is captured to the control unit. Then, the control unit performs decoding and encoding, and transmits the related information to the wearer wearing the intelligent nursing care device and the monitoring terminal held by the related family member end.

Figure 7:
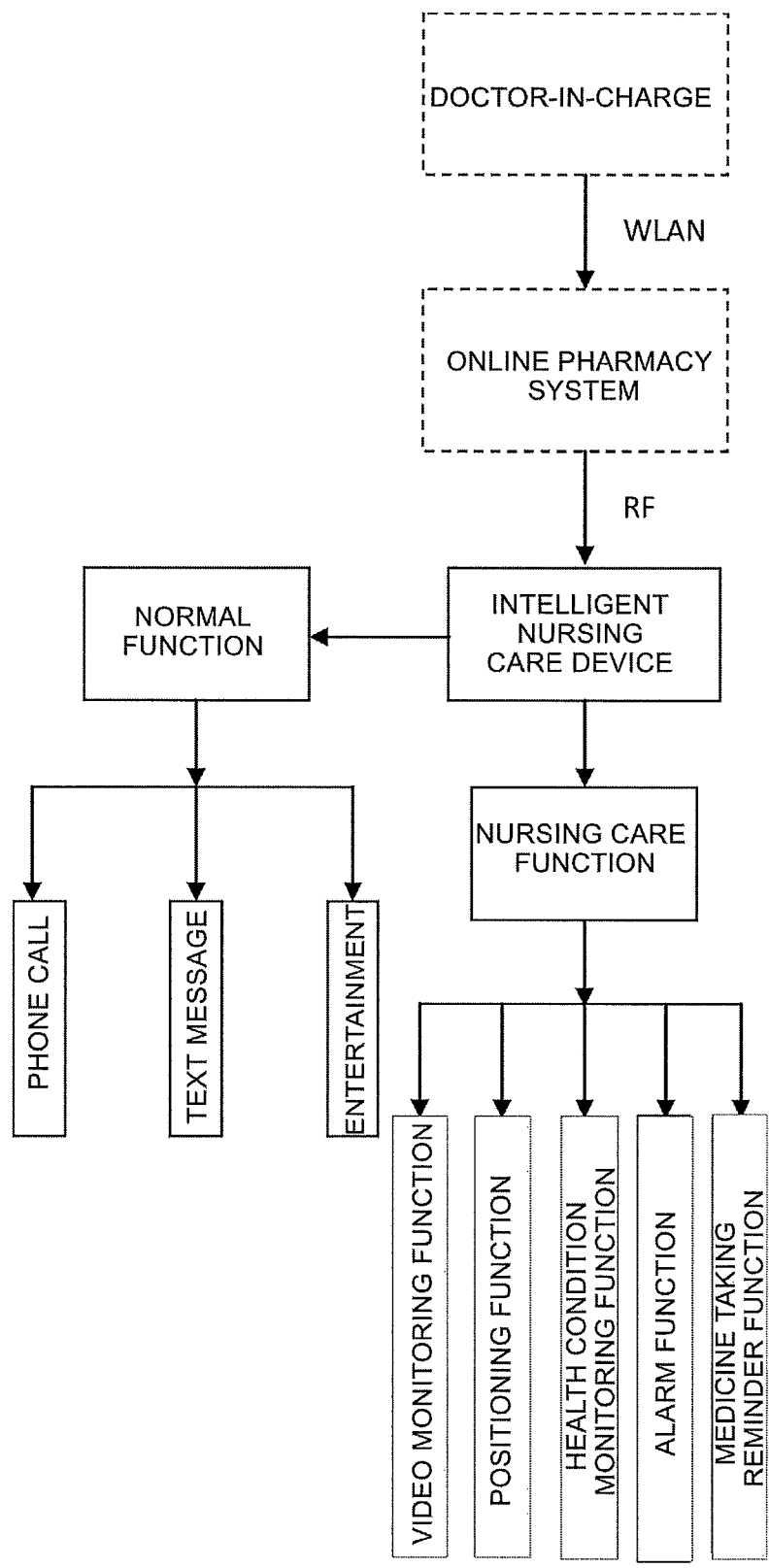
FIG. 7 is a block diagram showing a functional configuration of an intelligent nursing care device according to an embodiment of the present disclosure.

As described above, the intelligent nursing care device provided by the present embodiment can provide the nursing care device by above-described configuration, and can further provide normal functions, such as making a phone call, sending a text message, entertainment function. A block diagram of the intelligent nursing care device is shown in FIG. 7. The intelligent nursing care device can acquire the prescription from the doctor-in-charge via the online pharmacy system. This acquirement of the prescription is achieved by a wireless network communication method, such as WLAN. The online pharmacy system is achieved by a digital information management system, and the prescription is transmitted to the intelligent nursing care device via the RF module in order to provide the nursing care function. The nursing care function specifically includes a video monitoring function provided by the camera, a positioning function provided by the GPS, a health condition monitoring function provided by the biosensor, an alarm function provided by the speech generation device, a medicine dosage reminder function or the like.

As described above, the embodiment of the present disclosure provides an intelligent nursing care terminal to the elderly people according to a characteristic and actual situation of the elderly people. The intelligent nursing care terminal is wearable by the user. Thus, the position information and the health condition information of the wearer can be monitored in real time. Further, based on these multiple kinds of information, a safety warning reminder can be provided to the elderly people, and a medicine taking reminder can be provided to the wearer via the cloud server in order to secure a medicine taking safety of the elderly people. Further, the navigation function is provided to the user so that the elderly people are guided by the navigation function and avoid get-lost of the elderly people.

It is to be understood that above-described embodiments are used to explain the present disclosure, but not intend to limit the present disclosure. Obviously, those skilled in the art can change and modify present disclosure in various ways without departing from a spirit and a scope of the present disclosure. Thus, when the change and modification of the present disclosure belong to a scope of the claims of the present disclosure and their equivalents, the present disclosure also intends to include these changes and modifications.

What is claimed is:

1. An intelligent nursing care device, the intelligent nursing care device being a wearable nursing care device, comprising:
a monitoring unit that acquires position information and health condition information of a wearer in real time; and
a control unit that determines, based on the position information and the health information acquired by the monitoring unit, whether the position information exceeds a predetermined safety distance range, and a health condition of the wearer, and transmits a determination result to at least one of a cloud server and a monitoring terminal;
the intelligent nursing care device further comprising an online pharmacy unit comprising a communication module and a display panel,
wherein the online pharmacy unit communicates with a remote pharmacy system via the communication module, and displays a medicine dosage instruction provided by the remote pharmacy system on the display panel, and the medicine dosage instruction comprises a medicine type, amount, a medicine taking time, and a medicine taking frequency;
the online pharmacy unit further comprises a speech generation device, the online pharmacy unit determines, based on an actual dosage situation acquired by a camera of the monitoring unit, whether the actual dosage situation coincides with the medicine dosage instruction displayed on the display panel, and
when the actual dosage situation does not perfectly coincide with the medicine dosage instruction, the speech generation device outputs a notification speech until the actual dosage situation perfectly coincides with the medicine dosage instruction.

2. The intelligent nursing care device according to claim 1, wherein
the monitoring unit comprises an electronic fence and a biosensor,
the electronic fence comprises a camera and a positioning module, and the electronic fence acquires in real time the position information of the wearer at a current time, and
the biosensor monitors a human body of the wearer in order to acquire the health condition information of the wearer.

3. The intelligent nursing care device according to claim 2, wherein
the biosensor is disposed on a back plate that is directly contacted with the human body, and the health condition information is acquired in real time via the biosensor.

4. The intelligent nursing care device according to claim 2, wherein
the control unit determines the position information acquired by the positioning module, when determining that the position information exceeds the predetermined safety distance range, the control unit generates a first alarm signal, and
the control unit further compares the health condition information acquired by the biosensor with a normal health index stored in a database, when the health condition information exceeding the normal health index, the control unit generates a second alarm signal.

5. The intelligent nursing care device according to claim 4, wherein
the control unit outputs a warning tone simultaneously with a generation of the first alarm signal, and
after generating the second alarm signal, the control unit automatically transmits the health condition information at the current time to the cloud server and the monitoring terminal.

6. The intelligent nursing care device according to claim 5, wherein
when the control unit does not generate the second alarm signal, the control unit periodically transmits the health condition information acquired by the biosensor to the cloud server, and the control unit communicates with the cloud server in a wireless manner.

7. The intelligent nursing care device according to claim 2, wherein
the positioning module further has a navigation function, and
when acquiring the position information of the wearer at the current time and a destination together with the camera, the positioning module provides a scheduled route that guides the wearer to the destination based on the position information of the wearer at the current time.

8. The intelligent nursing care device according to claim 2, wherein the positioning module acquires the position information of the wearer at the current time, and the position module takes a screenshot of an image taken by the camera and periodically transmits the screenshot to the monitoring terminal.

* * * * *